United States Patent [19]

Adams, Jr.

[11] 4,217,293
[45] Aug. 12, 1980

[54] STABILIZED MANEB AND PREPARATION THEREOF

[75] Inventor: John B. Adams, Jr., Hockessin, Del.

[73] Assignee: E. I. Du Pont de Nemours and Company, Wilmington, Del.

[21] Appl. No.: 26,201

[22] Filed: Apr. 2, 1979

Related U.S. Application Data

[63] Continuation-in-part of Ser. No. 935,507, Aug. 21, 1978, abandoned.

[51] Int. Cl.² .............................................. C07F 13/00
[52] U.S. Cl. .................................................. 260/429 K
[58] Field of Search ..................... 260/429 K; 424/286

[56] References Cited

U.S. PATENT DOCUMENTS

| | | | |
|---|---|---|---|
| 2,848,297 | 8/1958 | Hill | 424/286 |
| 3,085,042 | 4/1963 | Luginbuhl | 424/286 |
| 3,173,832 | 3/1965 | Harris | 424/286 |
| 3,856,836 | 12/1974 | Boogaart et al. | 260/429 K |

FOREIGN PATENT DOCUMENTS 2335616  1/1974  Fed. Rep. of Germany .
48-43102 12/1973  Japan .

OTHER PUBLICATIONS

Donev, Khimiya i industriya (Sofia), 41, 100–101 (1969) No. 3.

*Primary Examiner*—Helen M. S. Sneed

[57] ABSTRACT

Manganese(II) ethylenebis(dithiocarbamate) of low ethylenethiourea content and its preparation by mixing disodium ethylenebis(dithiocarbamate) with formaldehyde in aqueous medium then mixing a water-soluble manganese(II) salt to precipitate the maneb. The product can be further formulated with a metal salt and also with paraformaldehyde.

10 Claims, No Drawings

STABILIZED MANEB AND PREPARATION THEREOF

CROSS REFERENCE TO RELATED APPLICATIONS

This application is a continuation-in-part of copending application Ser. No. 935,507, filed Aug. 21, 1978, now abandoned.

BACKGROUND OF THE INVENTION

Manganese(II) ethylenebis(dithiocarbamate) (maneb) is an important fungicide. The compound, however, is unstable and will tend to decompose, particularly at elevated temperatures.

Decomposition products, such as ethylenethiourea (ETU), can be found in freshly made maneb, and their concentrations will increase during storage. Although much work has been done to improve the stability and fungicidal activity of maneb, there are no known references which teach a method for reducing the ETU content of maneb.

L. Donev [Khimiyai industriya (Sofia) 41, 100–101 (1969), No. 3], for example, teaches a method of preparing maneb of increased dithiocarbamate content in which aqueous formaldehyde is added to a manganese(II) sulfate solution. Then a solution of ammonium ethylenebis(dithiocarbamate) (amobam) is added to precipitate the maneb. ETU concentration is not discussed.

U.S. Pat. No. 3,856,836 discloses a maneb derived from a formaldehyde-treated reaction mixture. The maneb is precipitated in aqueous medium from a water-soluble salt of ethylenebis(dithiocarbamic acid) and a water-soluble manganese(II) salt. Formaldehyde is added to the reaction mixture after precipitation. The reference does not discuss ETU concentration.

SUMMARY OF THE INVENTION

It has now been discovered that maneb having an unexpectedly low ETU content, both initially and after periods of storage, can be made by (1) mixing formaldehyde with disodium ethylenebis(dithiocarbamate) (nabam) in aqueous medium and then (2) mixing the formaldehyde-treated nabam with a water-soluble manganese(II) salt to precipitate maneb. The potassium analog of nabam may also be employed in the process of this invention. It is to be understood that the term "nabam" as used herein includes the potassium analog. According to this invention, maneb can be precipitated by: simultaneously adding aqueous solutions of formaldehyde-treated nabam and manganese(II) salt to a heel or common body of water ("heel process"); alternatively, an aqueous solution of manganese(II) salt can be added to an aqueous solution of formaldehyde-treated nabam ("batch process"); finally, an aqueous solution of formaldehyde-treated nabam can be added to an aqueous solution of manganese(II) salt ("reverse batch process"). The preferred method is the "heel process". Optionally, a dispersant can be added to the aqueous medium prior to precipitation.

DETAILED DESCRIPTION OF THE INVENTION

In the process of this invention, the amount of formaldehyde employed for each mole of nabam can range from about 0.2 and 1.0 mole, with preferred amounts of 0.4 to 0.6 mole, and the most preferred amount 0.5 mole. Smaller amounts of formaldehyde than the most preferred can be used with less effect, and larger amounts with increased risk of producing air-sensitive maneb, that is maneb wherein decomposition is markedly accelerated by contact with air. The concentration of the formaldehyde reagent can vary widely (e.g., 1–100%); however, commercially available formaldehyde solutions (e.g., 25–50%) are quite satisfactory.

The temperature of the nabam-formaldehyde aqueous solution can range from ambient (lower if desired) to the usual temperatures of freshly prepared nabam (e.g., 40°–45° C.). The time required for the formaldehyde-nabam solution to stand before maneb precipitation is short (no more than ten minutes at ambient temperatures), while it can stand for a week or so if desired. However, nabam in solution itself is not indefinitely stable and overly long storage periods are undesirable.

The maneb obtained by following the process of this invention tends to have a larger particle size than maneb produced from plain nabam. It may be desirable, therefore, to precipitate the maneb in the presence of a dispersant which will cause the maneb to form and remain as small particles. Small-particle maneb can then be formulated with little or no further grinding. Suitable dispersants include ligninsulfonate type dispersants such as Polyfon ® H (a sodium lignosulfonate produced by Westvaco Chemical Division, N. Charleston, S.C.). The amount of dispersant employed in the process of this invention can range from about 0.1% to 10% by weight of the reaction mixture.

The maneb damp cake obtained (e.g., by filtration) by the present process is of exceptionally low ETU content and easily filtered off and dried. The initial ETU content of the maneb product can be further reduced by treating the maneb damp cake with an aqueous solution of a heavy-metal salt (e.g. zinc chloride, copper(II) sulfate, manganese(II) sulfate). Use of a zinc salt produces a complex of zinc and maneb (hereafter referred to as mancozeb) with low ETU content. [For a description of mancozeb and maneb, see Pesticide Manual, 5th Edn. edited by H. Martin and C. R. Worthing, issued by the British Crop Protection Council, pages 328 and 329; also for mancozeb, see U.S. Pat. No. 3,379,610 (C. B. Lyon et al.)]. As used herein, the term "maneb" shall include mancozeb when the maneb or a portion thereof has been converted to mancozeb.

The maneb made by the process of this invention can be formulated by known methods for fungicidal formulations containing various agents, e.g., dispersants, wetting agents, paraformaldehyde, hexamethylenetetramine, heavy-metal salts (such as zinc chloride, copper-(II) sulfate and zinc sulfate).

Descriptions of formulation methods may be found in U.S. Pat. Nos. 2,504,406; 2,710,822; 2,778,768; 2,870,058; 2,974,156; 3,293,126; 3,379,610 and 3,497,598.

The following examples illustrate this invention. All parts and percentages are by weight and all temperatures are in degrees centigrade unless otherwise noted.

EXAMPLE 1

To 1115 g (1 mole) of 23% aqueous nabam at about 25° is added 40.6 g (0.5 mole) of 37% aqueous formaldehyde (Fisher Scientific Co., No. F-79). After standing for one hour the nabam solution is added during 22 minutes to 1160 ml of stirred water kept at 35°, at the same time with a solution of 169 g (1 mole) of manganese(II) sulfate monohydrate in 486 ml of water, with the manganese(II) sulfate solution in a manner such that the molar fraction of manganese(II) sulfate in the mixture is generally greater than the molar fraction of nabam. The mixture is stirred for an additional ten minutes at 35°.

The maneb is filtered off and washed on the filter with 1200 ml of water, then with about 200 ml of 7% zinc chloride solution. The damp cake is dried in a vacuum oven, for an hour at 65° with high vacuum, then under a nitrogen stream at 37° overnight. Into the dried maneb is blended 1% paraformaldehyde powder, and the product is bottled.

ETU assays on the product stored at room temperature for the indicated time are as follows:

| Days of Storage Time | ppm ETU |
| --- | --- |
| 0 | 10–20 |
| 28 | 214 |
| 62 | 256 |
| 97 | 102 |
| 127 | 60 |

EXAMPLE 2

(a) Into stirred water (116 ml) kept at 35° is added simultaneously 112 g (0.1 mole) of 23% aqueous nabam and 15.1 g (0.1 mole) of 23% aqueous manganese(II) sulfate, the solutions being added during a 25-minute period. After an additional ten minutes of stirring at 35°, the mixture is filtered and the maneb washed with water and dried. This is maneb "2a".

(b) The reaction (a) is repeated except that 0.05 mole of formaldehyde (as a 37% formaldehyde solution) is added to the 0.1 mole aqueous nabam. Ten minutes later the aqueous nabam-formaldehyde is added to water simultaneously with 0.1 mole manganese(II) sulfate to start the maneb precipitation. The product obtained is maneb "2b", an exemplary product of the present invention.

The maneb "2a" and maneb "2b" are assayed for ETU, with the following results:

| Maneb Sample | ppm ETU (No aging) |
| --- | --- |
| 2a | 175 |
| 2b | 41 |

EXAMPLE 3

(a) Into 100 ml of 1 M aqueous manganese(II) sulfate, swirled in a 500 ml Erlenmeyer flask, is poured 100 ml of 1 M aqueous nabam. The mixture is swirled for two minutes, then filtered and the maneb washed with water and dried. This is maneb "3a".

(b) The reaction (a) is repeated except that 0.05 mole of formaldehyde (as 37% formaldehyde solution) is added to the nabam solution ten minutes prior to the start of maneb precipitation. The product obtained is maneb "3b", an exemplary product of the present invention.

The maneb "3a" and maneb "3b" are assayed for ETU, with the following results:

| Maneb Sample | ppm ETU (No aging) |
| --- | --- |
| 3a | 721 |
| 3b | 265 |

EXAMPLE 4

Into 1160 ml of stirred water kept at 25° and under a nitrogen blanket is added 15.2 g. of Polyfon ® H, followed by simultaneous addition of 723 g. of 23% manganese(II) sulfate and a nabam/formaldehyde solution (40.6 g of 37% formaldehyde plus 1115 g. of 23% nabam, let stand 45 minutes), during a 50-minute period. After an additional 10 minutes, the mixture is filtered and the maneb washed on the filter with water and 7% zinc chloride solution. The damp cake is dried in a 37° % vacuum oven under a nitrogen sweep for 63 hours.

The product is assayed for ETU with the following results:

| Maneb Sample | ppm ETU | Days of Storage Time |
| --- | --- | --- |
| 4 | 24 | 3 |
|   | 9 | 19 |

What is claimed is:

1. A process for preparing a stabilized maneb of low ethylenethiourea content which comprises the steps of mixing nabam with formaldehyde in aqueous medium and then mixing the formaldehyde-treated nabam with a water-soluble manganese(II) salt to precipitate the maneb.

2. A process for preparing a stabilized maneb of low ethylenethiourea content which comprises the steps of mixing nabam with formaldehyde in aqueous medium then mixing the formaldehyde-treated nabam with a water-soluble manganese(II) salt to precipitate the maneb, treating the maneb with an aqueous solution of a salt selected from zinc, manganese and copper, drying the maneb and then blending paraformaldehyde into the dried maneb.

3. A process of claim 1 or 2 wherein the formaldehyde is from 0.2 to 1.0 mole per mole of nabam.

4. A process of claim 1 or 2 wherein the formaldehyde is from 0.4 to 0.6 mole per mole of nabam.

5. A process of claim 1 or 2 wherein the concentration of the formaldehyde reagent is 1 to 100%.

6. A process of claim 1 or 2 wherein maneb is precipitated by adding the aqueous solutions of formaldehyde-treated nabam and a manganese(II) salt to a heel of water substantially simultaneously.

7. A stabilized maneb of low ethylenethiourea content prepared by the process which comprises mixing nabam with formaldehyde in aqueous medium then mixing the formaldehyde-treated nabam with a water-soluble manganese(II) salt to precipitate the maneb.

8. A stabilized maneb of low ethylenethiourea content prepared by the process which comprises mixing nabam with formaldehyde in aqueous medium then mixing the formaldehyde-treated nabam with a water-soluble manganese(II) salt to precipitate the maneb, treating the maneb with an aqueous solution of a zinc salt, drying the maneb and then blending paraformaldehyde into the dried maneb.

9. The process of claim 1 or 2 in which the formaldehyde-treated nabam is mixed with the water-soluble manganese(II) salt in the presence of a dispersant.

10. The stabilized maneb of claim 7 or 8 in which the formaldehyde-treated nabam is mixed with the water-soluble manganese(II) salt in the presence of a dispersant.